(12) United States Patent
Bath

(10) Patent No.: US 7,858,103 B2
(45) Date of Patent: Dec. 28, 2010

(54) METHOD FOR DEFINING, IDENTIFYING AND ISOLATING FATTY ACID AND RETINAL BINDING PROTEIN COMPLEXES HAVING IMMUNO-SUPPRESSIVE ACTIVITY

(76) Inventor: Jennifer L. Bath, 1139 5th St. North, Fargo, ND (US) 58102

( * ) Notice: Subject to any disclaimer, the term of this patent is extended or adjusted under 35 U.S.C. 154(b) by 2484 days.

(21) Appl. No.: 10/292,931

(22) Filed: Nov. 13, 2002

(65) Prior Publication Data

US 2005/0058997 A1    Mar. 17, 2005

(51) Int. Cl.
*A61K 39/00* (2006.01)
*A61K 45/00* (2006.01)
*C07K 14/00* (2006.01)

(52) U.S. Cl. .................. 424/269.1; 424/278.1; 530/350

(58) Field of Classification Search ........................ None
See application file for complete search history.

(56) References Cited

PUBLICATIONS

NCBI AAK57805 http://www.ncbi.nlm.nih.gov/protein/14289131; accessed 2009.*

NCBI AAK57805-revision history http://www.ncbi.nlm.nih.gov/entrez/sutils/girevhist.cgi?val=AAK57805&log$=seqview; accessed 2009.*

Hoselton et al. (Parasite Immunology, 2002; 24: 429-435).*

Tang et al. (International Journal for Parasitology, 1995; 25(7): 847-851 and 858).*

* cited by examiner

*Primary Examiner*—Vanessa L Ford
*Assistant Examiner*—Lakia J Tongue
(74) *Attorney, Agent, or Firm*—Campbell Nelson Whipps LLC

(57) ABSTRACT

A method for defining, identifying and isolating recombinantly produced protein complex is provided. The protein complex comprises a group of fatty acid and retinol-binding proteins wherein the complex protein structure is entirely alpha-helical. The molecular weight of the recombinant protein is approximately 46 kDa comprised of 26 kDa GST and 20 kDa Hp20 protein. The procedures for extracting, isolating and analyzing the recombinantly in vivo produced protein complex and Hp20 protein of the recombinantly in vivo produced protein complex are provided.

1 Claim, 8 Drawing Sheets

Figure 1: SDS-PAGE
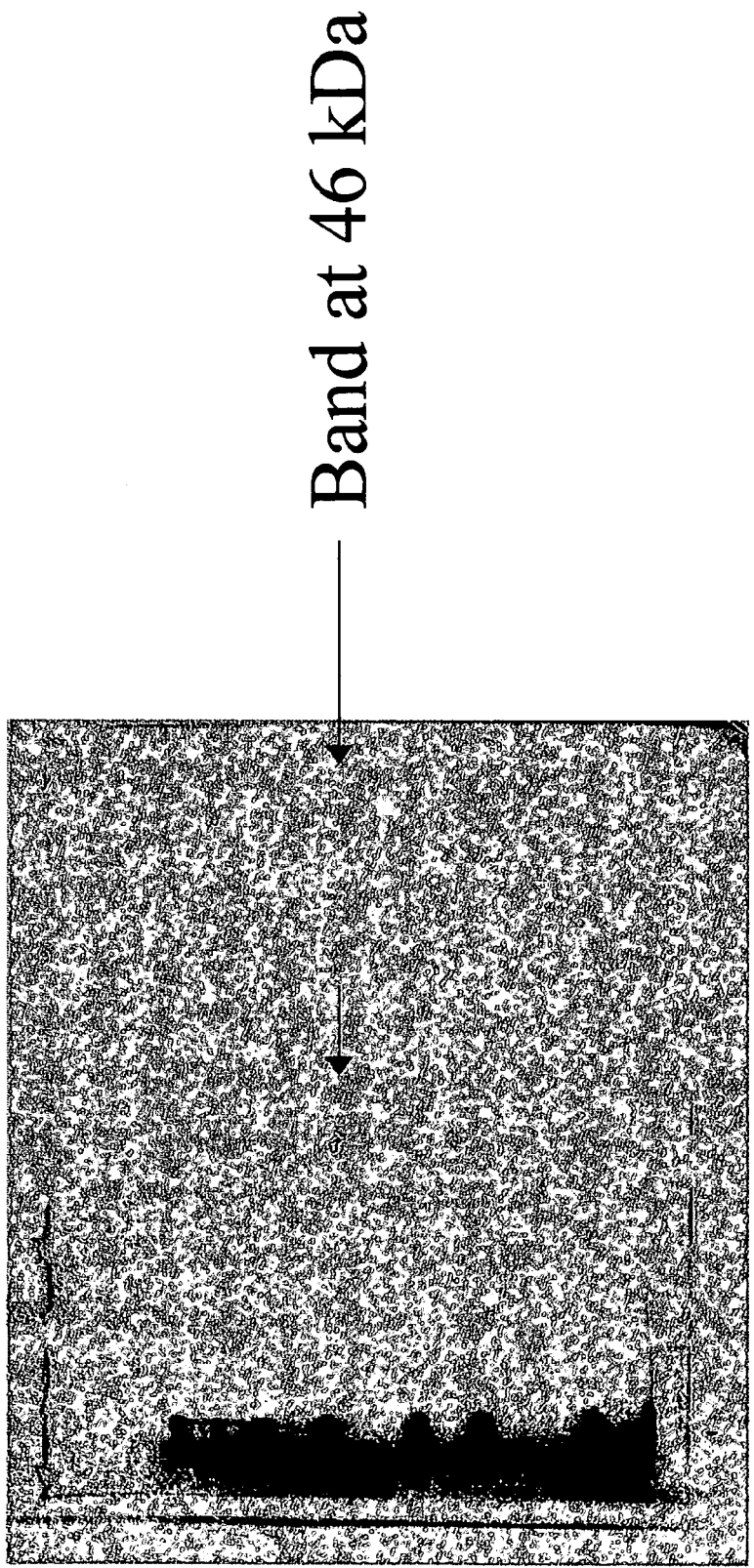

Figure 2: Analysis of Hp20 Protein Structure Showing Hp20 Protein Structure is entirely Alpha-Helical, Arranged as a Helix.

| | | | | | | |
|---|---|---|---|---|---|---|
| M | C | F | C | | K | H |
| L | C | T | C | | K | H |
| R | C | P | C | | V | E |
| L | C | A | C | | A | E |
| G | C | E | H | | T | C |
| F | C | K | H | | L | C |
| L | E | K | H | | S | C |
| A | E | V | H | | P | C |
| L | E | I | H | | E | C |
| L | E | E | H | | S | C |
| I | E | E | H | | K | H |
| V | E | F | H | | A | H |
| C | E | F | H | | F | H |
| V | E | N | H | | F | H |
| C | E | E | H | | D | H |
| S | C | K | H | | K | H |
| T | C | F | H | | V | H |
| P | C | K | H | | Q | H |
| I | C | T | H | | S | H |
| K | C | E | H | | S | H |
| K | C | D | H | | L | H |
| A | C | E | H | | K | H |
| E | C | A | H | | D | H |
| D | C | L | H | | L | H |
| I | C | N | H | | H | H |
| P | C | F | H | | K | H |
| Q | H | F | H | | Q | E |
| E | H | K | H | | I | E |
| V | H | E | H | | L | E |
| R | H | K | H | | V | E |
| E | H | S | H | | G | C |
| V | C | P | C | | D | C |
| L | C | S | H | | | |
| P | C | L | H | | | |
| E | H | Y | H | | | |
| N | H | A | H | | | |
| V | H | K | H | | | |
| V | H | I | H | | | |
| Q | E | E | H | | | |
| L | E | N | H | | | |
| I | E | L | H | | | |
| L | E | R | H | | | |
| S | C | E | H | | | |
| | | I | H | | | |
| | | L | H | | | |
| | | K | H | | | |

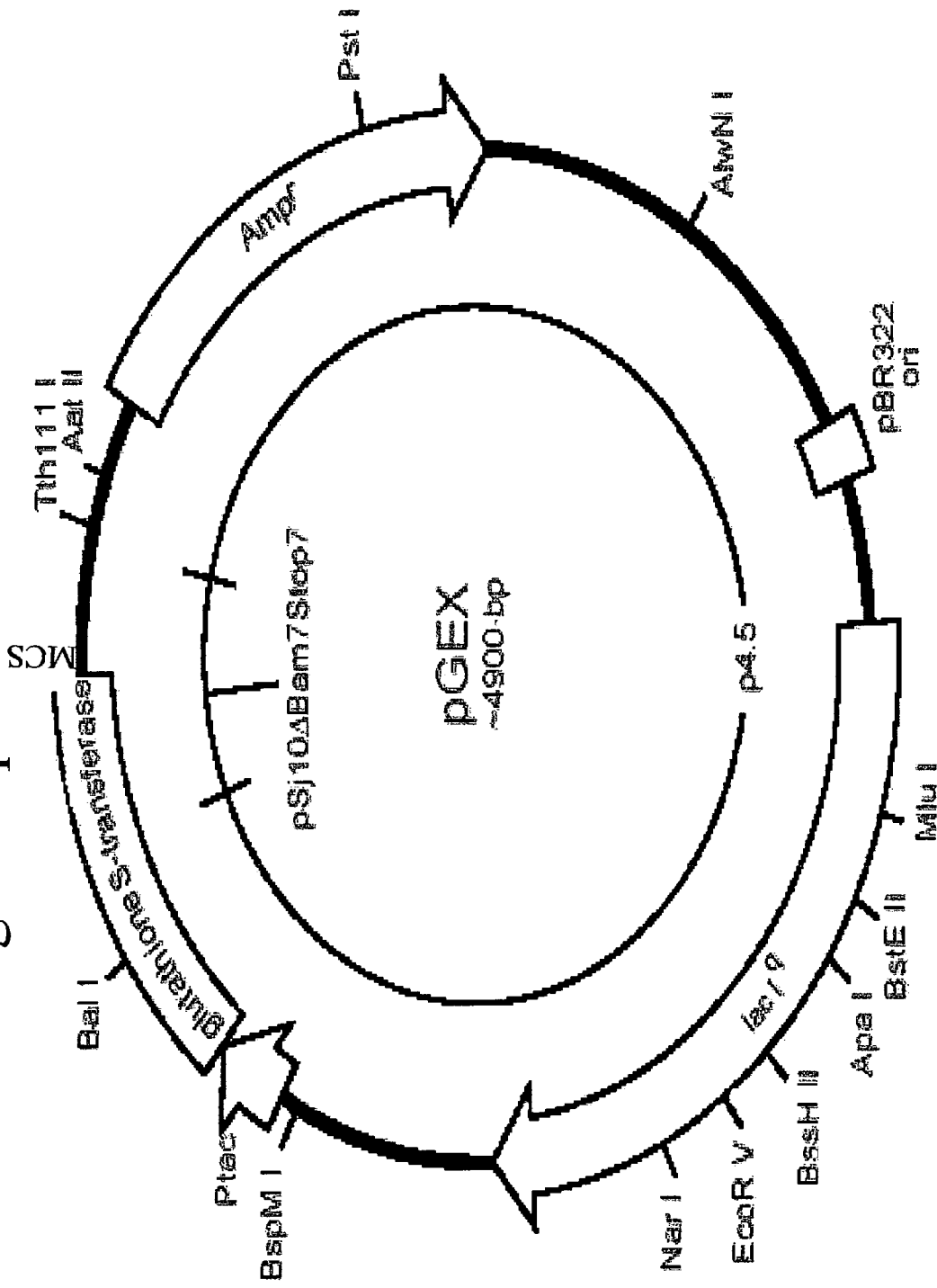
Figure 3: pGex-6P-2 Vector

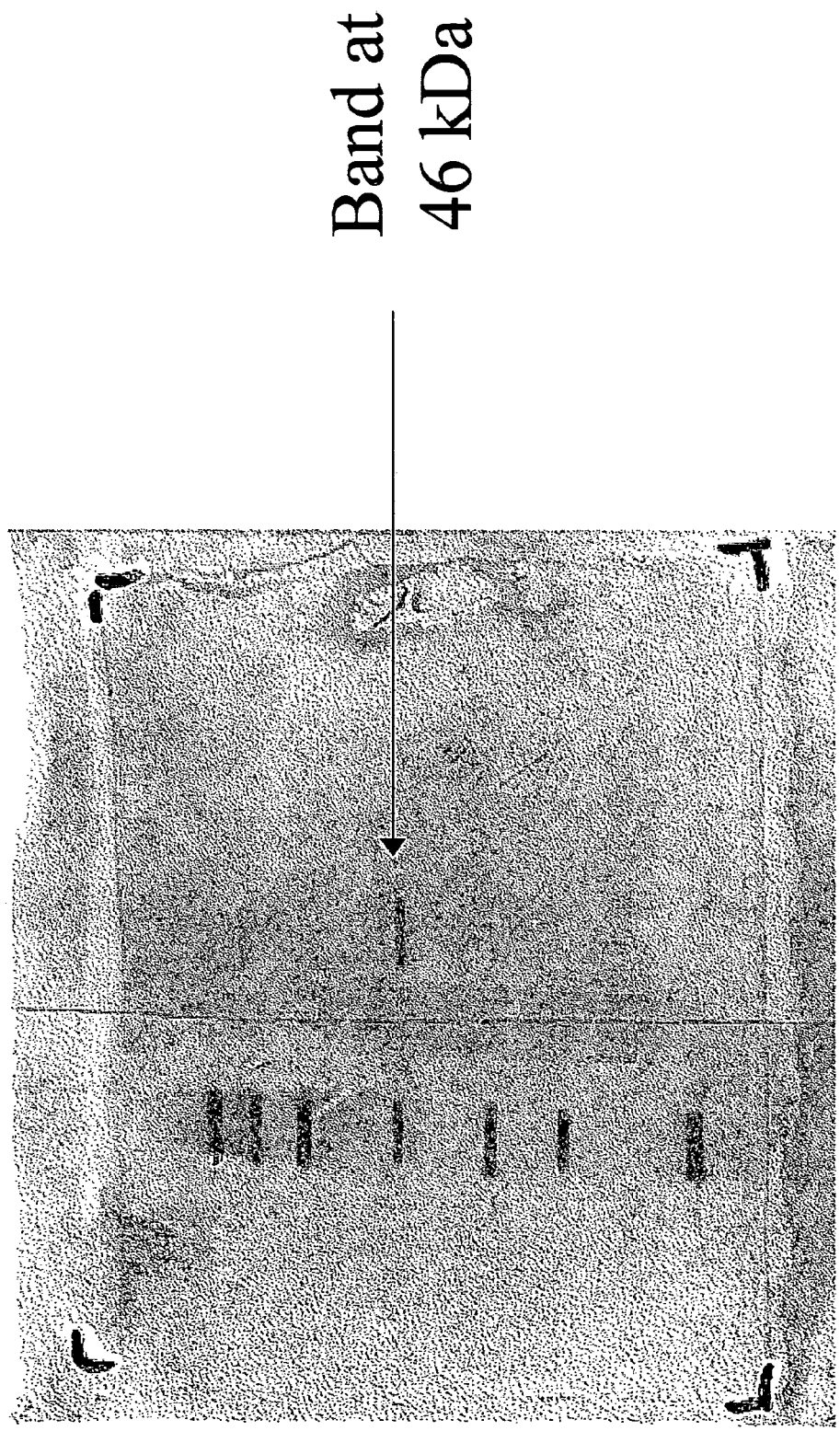
Figure 4: Western Blot

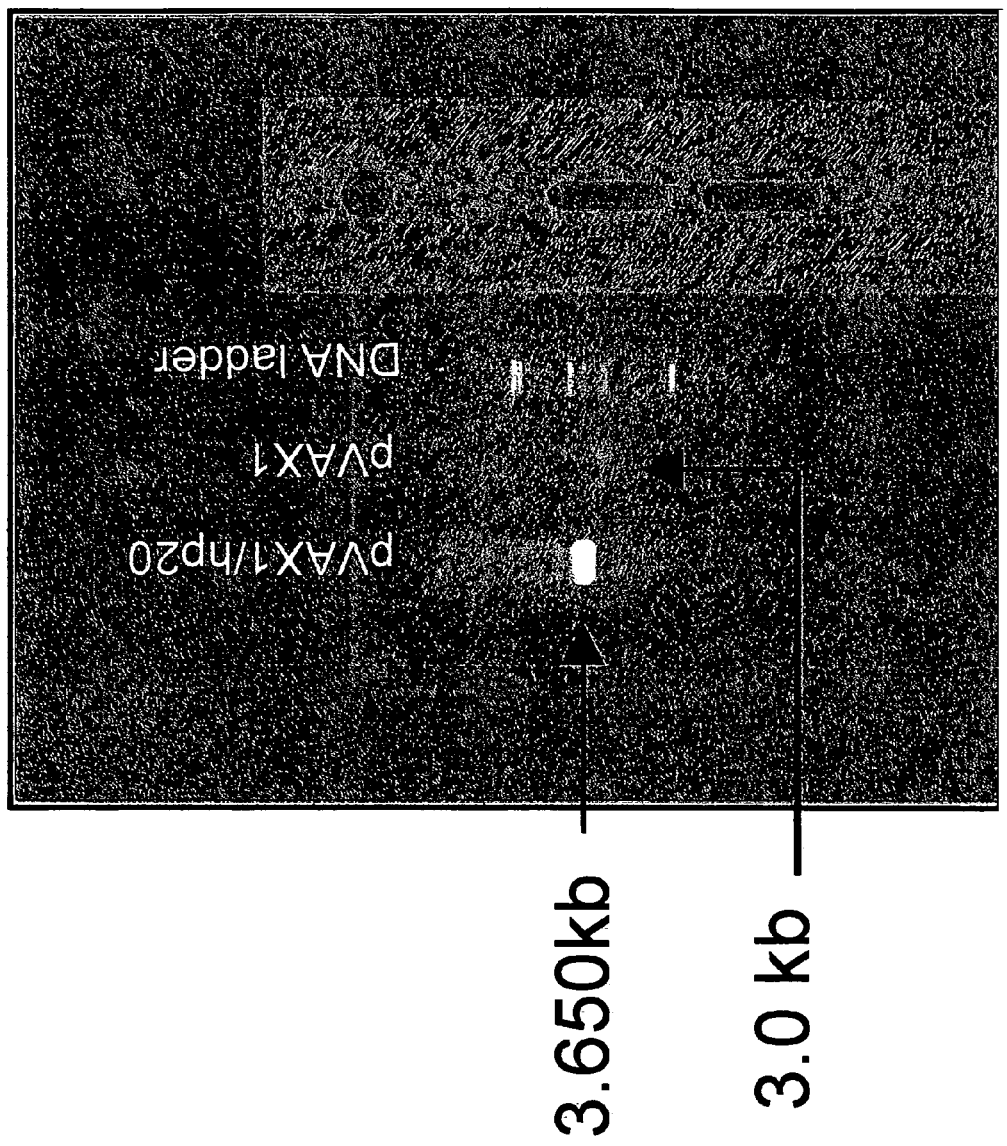
Figure 5: Agarose Gel Electrophoresis

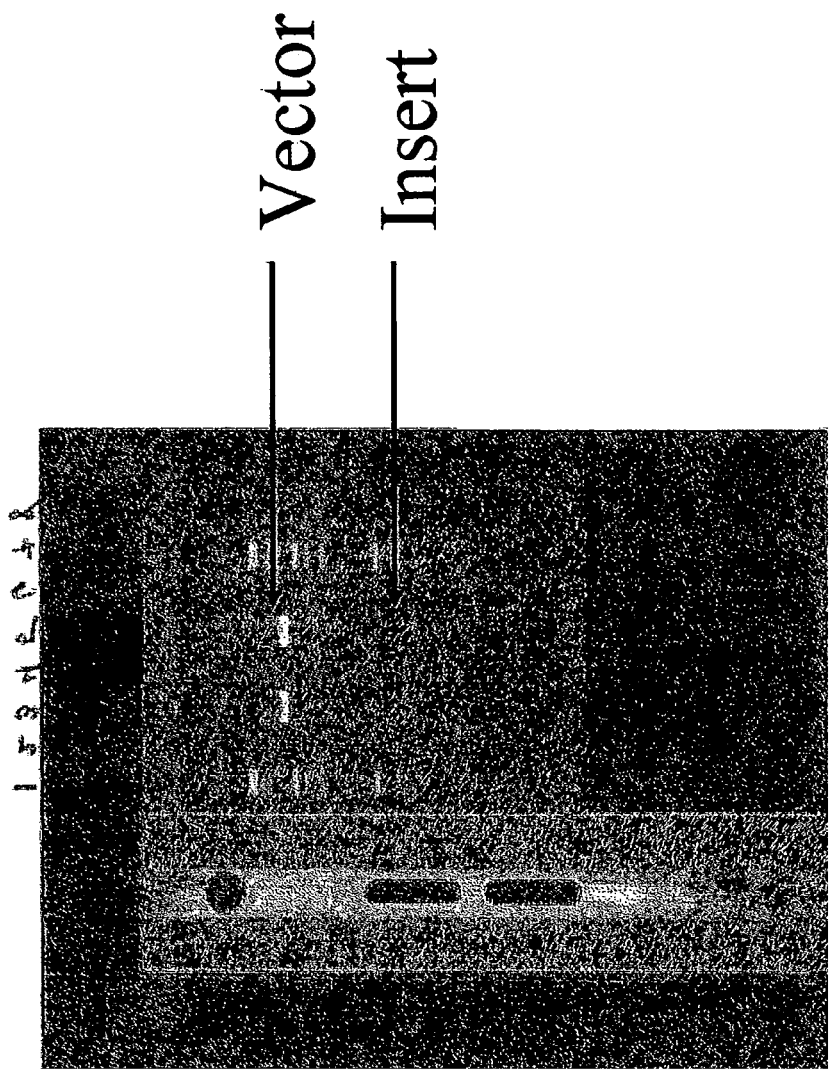
Figure 6: hp20 insert

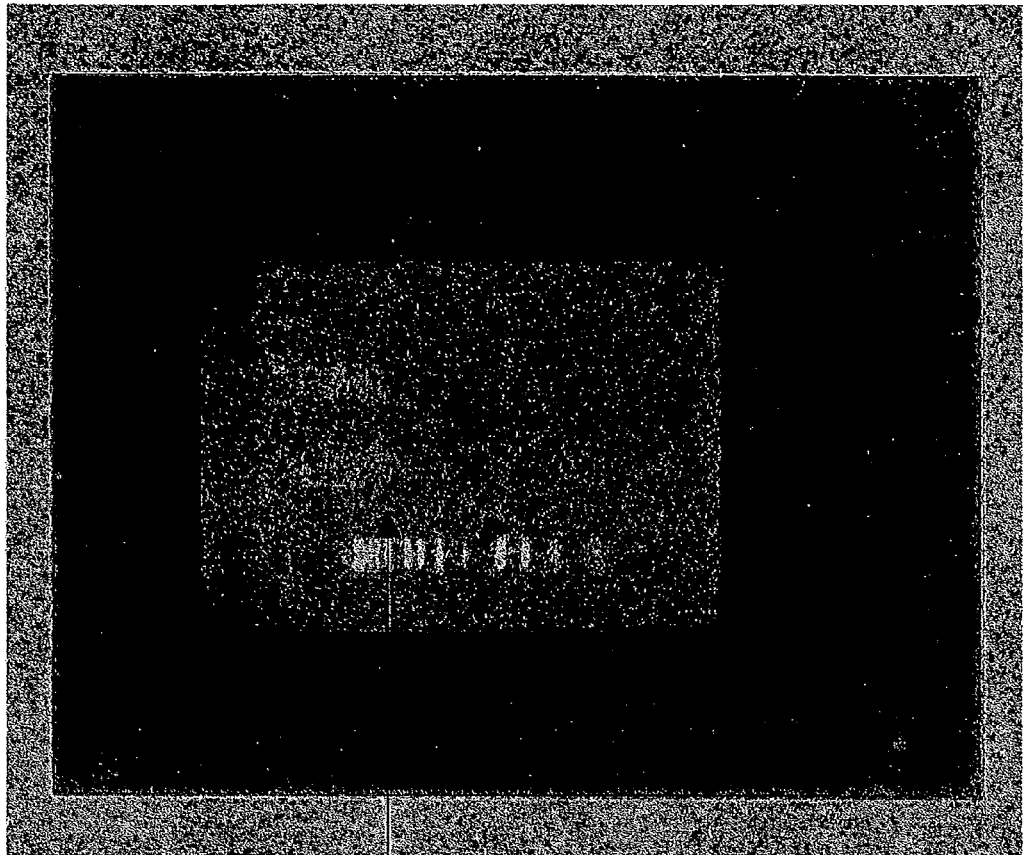
Figure 7: pGEX/hp20 Construct
Demonstrating successful ligation of hp20 to pGEX

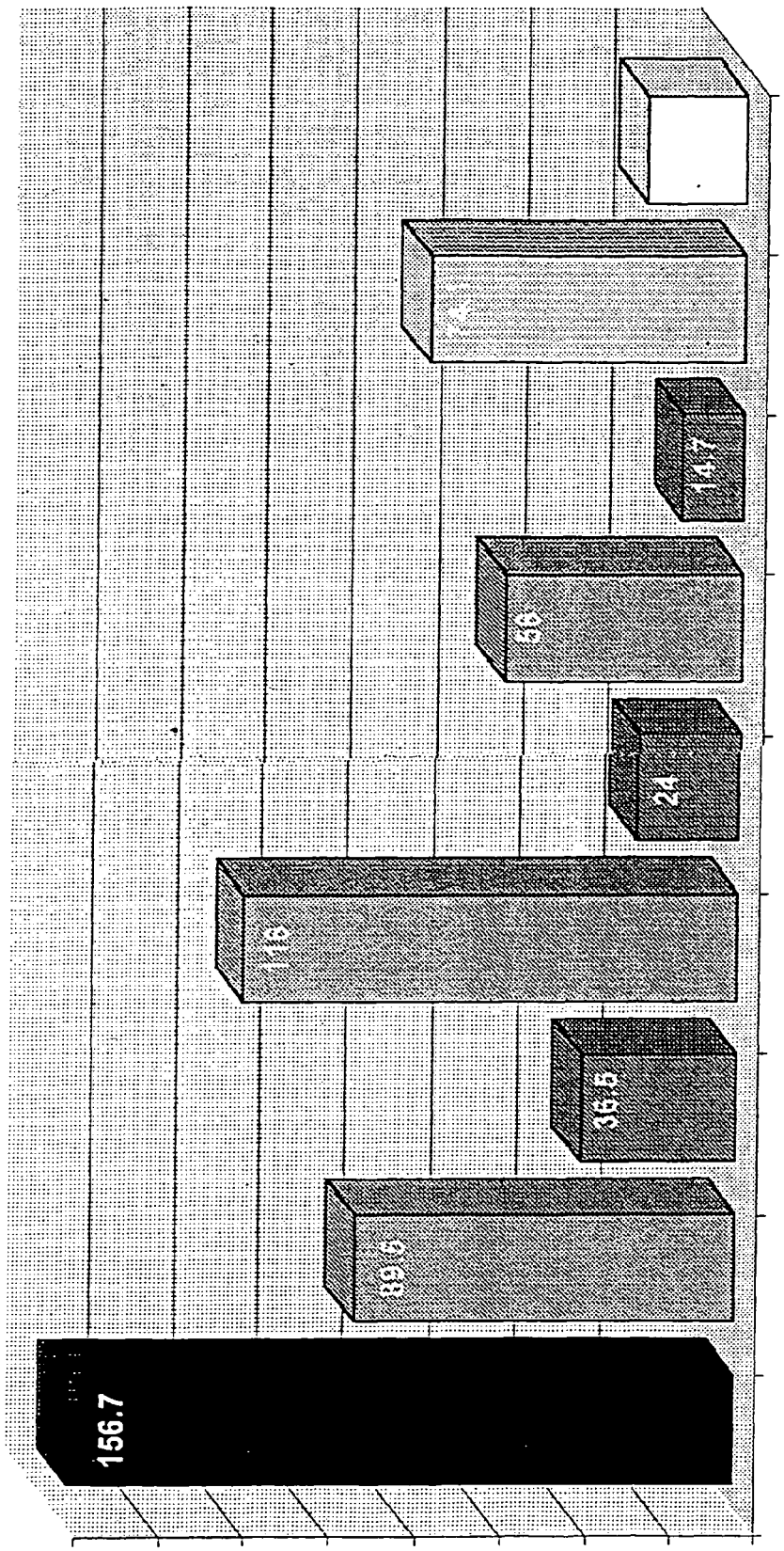

METHOD FOR DEFINING, IDENTIFYING AND ISOLATING FATTY ACID AND RETINAL BINDING PROTEIN COMPLEXES HAVING IMMUNO-SUPPRESSIVE ACTIVITY

FIELD OF THE INVENTION

The present invention is in the fields of molecular biology and protein biochemistry. The invention relates generally to a method for defining, identifying and isolating protein complexes having in vivo immuno-suppressive activity and protein molecules so extracted and isolated. More specifically, the invention relates to methods and procedures for separating and analyzing a protein molecule having immuno-suppressive activity from a parasite having an immunomodulatory factor that down regulates the in vivo host immune response, and the protein molecule obtained thereby.

BACKGROUND OF THE INVENTION

Researchers have long pointed out the fact that *H. polygyrus*, a nematode parasite, must produce a protein that effectively down regulates and suppresses the host's ability to mount an inflammatory response. It has also been known that nematode fatty acid and retinol-binding (FAR) proteins that are entirely alpha-helical in structure have been shown to bind fatty acids. FAR proteins have been shown to bind inflammatory mediators and their precursors. Inflammatory mediators act as signals to recruit or activate other cells. The role of inflammatory mediators is to alert host body cells to infection and to recruit them to mount an inflammatory response to help clear the infection. If a FAR protein is intercepting these mediators, the mediator signals never reach the cells that are being recruited. Therefore, the inflammatory response directed at clearing the parasitic infection is ablated. It is postulated that a FAR protein binding these inflammatory mediators would explain how *H. polygyrus* is able to survive in the host's intestines without being expelled (even in mice that have been repeatedly immunized or infected) and how chronic infections are formed and maintained without any significant damage to the larvae.

For decades, the literature regarding *H. polygyrus* has described an elusive immunomodulatory factor (IMF) that downregulates the host immune response. It is known that immunosuppression is present across both classes of nematodes. It has also been known that nematodes are able to cause these chronic infections but the means by which chronic infections are achieved remains controversial. For years, hypotheses have been proposed as to how intestinal helminths (parasitic nematodes) have been able to evade the host immune system. The main focus of research has been directed to immunomodulation, or down regulation of the host's immune system (immunosuppression), but to date progress has been slow.

To date, to the best knowledge of the inventor, no research group has been able to isolate or identify the unknown immunomodulatory protein from *H. polygyrus*. Researchers have postulated that any immunomodulatory proteins acting on the host's immune system are most likely released from the parasite as E/S proteins, that is, excretion proteins presently being excreted as useless or harmful to the nematode or secretion proteins present as a product or a release from the nematode to perform a function useful to the nematode.

Researchers have described the immunosuppression that is occurring in the presence of nematodes by demonstrating that many nematodes reside in tissue sites in a host surrounded by inflammatory cells but apparently unaffected by the presence of the inflammatory cells. For example, in one report, "in *H. polygyrus*, the $L_3$ and $L_4$ larvae develop in the muscularis externa of the mouse intestine for a period of 8-9 days before returning to the gut lumen as adults, in immune challenged mice, these sites of development become surrounded by inflammatory cells and despite the intensity of local cellular activity, few if any worms are actually killed within such foci of cellular activity. There is a very obvious stunting of worms and their capacity to survive in the gut lumen is greatly impaired once they have completed development. However, larvae can survive in such gramlomata for weeks and still succeed in returning to the gut lumen." Jerzy M. Behnke, Christopher J. Barnard, and Derek Wakelin. "Understanding Chronic Nematode Infections: Evolutionary Considerations, Current Hypotheses and the Way Forward." International Journal for Parasitology (Vol. 22, No. 7, 1992): 861-907.

Very little is known about nematode FAR proteins. What is known is that they appear to bind retinol (a vitamin A derivative) and certain fatty acids (most interestingly, inflammatory mediators and their precursors). The importance of these particular ligands, and the immunological aspects of *H. polygyrus* infection, make for a very interesting combination.

The Connection Between Retinol Binding and Immunity:

Firstly, it has been shown in order for a host to successfully 'clear' or 'rid itself' of an *H. polygyrus* infection, it must produce what is known as a Th-2 type immune response. This type of immune response, known as a humoral response (involving antibodies), is usually directed at extracellular organisms (those originating from outside the host's body). However, poor-responding mice have little or no ability to decrease worm burden or fight infection to *H. polygyrus* and mount a Th-1 type response instead. This type of immunity is referred to as cell-mediated immunity, and is usually reserved for fighting intracellular parasites (originating from inside a host cell; e.g. viruses or tumors). This Th-1 type response is ineffective at protecting the host from infection and thus the infection becomes chronic. It has been proposed the *H. polygyrus* produces an E/S protein which is able to 'switch' the Th-type of the response, or trick the host into producing a Th-1 type response which is not beneficial and allows the parasite to maintain the chronic infection. The link between retinol and a retinol binding protein (like a FAR protein) is able to explain this phenomenon. When a retinol binding protein binds retinol it sequesters the retinol, making it unavailable to the host. It has been shown retinol is in fact a costimulator of CD4+ T cells (the type of cell that determines the Th type of the response) and the CD4+ T cells cannot mount a functional Th-2 type response without retinol. This would effectively 'switch' the Th-type to a type 1. This, therefore, would explain the Th-type switching that we see during *H. polygyrus* infections and the subsequent chronicity of infection.

The Connection Between Fatty Acid Binding and Immunity:

Nematode FAR proteins have been shown to bind fatty acids that fall into the categories of inflammatory mediators and their precursors. Inflammatory mediators are signals released by cells that recruit or activate other cells. Their role is to alert other cells to infection and recruit them to mount an inflammatory response to help clear the infection. If a FAR protein is intercepting these mediators, the mediators never reach the cells being recruited and therefore the inflammatory response that should be directed at clearing the parasitic infection is ablated. Researchers have long pointed out the fact *H. polygyrus* must produce a protein that effectively downregulates and suppresses the host's ability to mount an inflammatory response. Unfortunately, no one has been able to produce a mechanism or identify a particular protein responsible (until now). A FAR protein binding these inflammatory mediators explains how *H. polygyrus* is able to survive in the host's intestines without being expelled (even in mice repeatedly immunized or infected) and how chronic infections are formed and maintained without any significant damage to the larvae (a phenomenon well documented, but still unexplained).

For decades now the literature regarding *H. polygyrus* has described an "elusive" immunomodulatory factor (IMF) that downregulates the host immune response. It is known that this immuno-depression is easily demonstrable across both classes of Nematoda. The potential chronicity of nematode infections is not disputed, but the means through which chronic infections are achieved has not been determined.

Researchers have agreed any immunomodulatory proteins in existence would be most likely found within the E/S proteins. However, researchers have had no idea of the relevant factors needed to be identified to identify or isolate the immunomodulatory protein that downregulates the host's immune response.

Many of these studies directed to immunomodulatory proteins have turned to *H. polygyrus* as the primary model, for a number of reasons: 1) it is an excellent lab model; 2) it establishes chronic infections in many mouse strains; 3) there is a long history of research on this organism, as it was originally proposed as a model for human hookworm decades ago.

The majority of research performed on *H. polygyrus* has focused on the immunosuppression occurring. The downregulation described by many researchers fits into what would be expected by a FAR protein, that is, many nematodes seem to reside in tissue sites surrounded by inflammatory cells but apparently unaffected by their presence. This must be caused by localized suppression of the immune response and the cause of the suppression must be an E/S protein. An E/S protein is directed into the site of downregulated immunity because it is produced at the exact time during infection and is an E/S protein.

In the *H. polygyrus*, the $L_3$ and $L_4$ larvae develop in the muscularis externa of the mouse intestine for a period of 8-9 days before returning to the gut lumen of adults. In immune challenged mice, these sites of development become surrounded by inflammatory cells and despite the intensity of local cellular activity, few if any worms are actually killed within such foci of cellular activity. There is a very obvious stunting of worms and their capacity to survive in the gut lumen is greatly impaired once they completed development. However, larvae can survive such gramulomata for weeks and still succeed in returning to the gut lumen. Jerzy M. Behnke, Christopher J. Barnard, and Derek Wakelin. "Understanding Chronic Nematode Infections: Evolutionary Considerations, Current Hypotheses and the Way Forward." International Journal for Parasitology (Vol. 22, No. 7, 1992): 861-907.

*H. polygyrus* has been used as a model to demonstrate chronic infections caused by helminths. If this model does represent helminth infections in general, it may be possible to target more than just the nematodes closely related to *H. Polygyrus*, such as the *Trichostrongylus* species or the *Ancylostoma* hookworm which infects millions of individuals.

Because a FAR protein has to actually bind to its ligand to cause immunosuppression, the ligand therefore is a complexing agent with coordination bonding by means of a coordinating atom with electron pairs to donate or share, a procedure to inhibit the formulation of the chronic infection is to physically block the protein from binding its ligands. Two main methods may be used:

1) Antibody recognition of Hp20 protein. Antibodies produced by the host during an *H. polygyrus* infection can bird to both the native form and the recombinant form of Hp20 protein. The fact that the Hp20 protein is highly immunogenic causes it to be a target for antibody-mediated immunity. The treatment would involve the actual administration of antibodies during infection, or prophylactic treatment by immunization using the isolated Hp20 protein.

2) Drug-mediated targeting of Hp20 protein. A drug or protein designed to specifically block the active binding site of the Hp20 protein would prevent ligand binding.

The above description of the presence of nematodes in a host body and concomitant chronic infection has been known but the key as to how the parasite was managing to suppress the host immunity has not been known.

It is an object of the present invention to provide a key as to how the *H. polygyrus* manages to suppress the host immunity.

It is an object of the present invention to provide a method to target helminth infections of hosts in general.

It is an object of this invention to provide a method to target infections, chronic and acute, of nematodes closely related to *H. polygyrus* such as nematodes of the species *Trichostrongylus* or the *Ancylostoma* species, as well as other helminth infections.

It is an object of this invention to provide a method to target infections, chronic and acute, of nematodes, specifically *H. polygyrus*.

It is an object of this invention to define, identify and isolate protein complexes having immunosuppressive activity of a host's ability to mount an inflammatory response to the presence of a helminth.

It is an object of this invention to provide compositions of protein molecules having immunosuppressive activity, methods and procedures for identification, preparation, separation and analysis of such protein molecules.

It is an object of this invention to define, identify and isolate a protein molecule comprising a FAR-1 protein from *H. polygyrus* having immunosuppressive activity from a parasite.

SUMMARY OF THE INVENTION

A method is provided for defining, identifying and isolating a recombinantly produced protein complex. The protein complex comprises a group of fatty acid and retinol-binding proteins wherein the complex protein structure is entirely alpha-helical, the molecular weight of the recombinant protein is approximately 46 kDa comprised of 26 kDa GST and 20 kDa Hp20 protein, wherein the added protein for isolation of the Hp20 protein is glutathione-S-transferase (GST). A tertiary structure analysis of the Hp20 protein predicts the Hp20 protein is globular and compact. The amino acid sequence of the recombinant protein indicates the Hp20 protein has a leader sequence which allows the Hp20 protein to be released and is an excretory/secretory protein from the *H. polygyrus* nematode. The procedures for extracting, isolating, and analyzing the in vivo recombinantly produced protein complex and the identified Hp20 protein of the recombinantly produced protein complex are provided.

DESCRIPTION OF THE DRAWINGS

FIG. 1 illustrates the confirmation of the molecular weight of the recombinant protein. Sodium dodecyl polyacrylamide gel electrophoresis (SDS-PAGE) of purified recombinant protein sample is illustrated which shows one band, at approximately 46 kDa, representing the recombinant GST/Hp20 fusion protein. Gel was stained with Bio-safe Commassie blue (bio-rad) and indicates that fusion protein is in purified form.

FIG. 2 illustrates that the Hp20 protein structure is entirely alpha-helical, arranged as a helix, as indicated by a computer program. (Secondary structure analysis ExPASy Proteomics tools). This secondary structure analysis provides results, by the programs definitions, demonstrating the protein is entirely alpha-helical in its structure. This is significant because it demonstrates that despite the unique amino acid sequence of Hp20 protein it has retained its alpha-helical structure. Such conservation of structure is highly indicative of the importance of the proteins structure in terms of its function, as well as the importance of the proteins function to survival of the parasite.

FIG. 3 illustrates the pGEX-6P-2 vector with the hp20 gene inserted in the pGEX vector in map of the pGEX-6P-2 vector genome. The multiple cloning site is shown, including the sites where the hp20 gene was cloned in (EcoR1 and Not1). The map also shows the tac promoter and all useful sites for cloning, induction and growth of the plasmid within a host.

FIG. 4 illustrates the western blot analysis which gave a positive result for the pGEX/Hp20 protein at 46 kDa, the western blot of the protein sample from FIG. 1, of purified recombinant GST/Hp20 protein. The western blot was probed with a commercially purchased goat-anti GST antibody to detect the GST portion of the fusion. The secondary antibody used was a commercially available donkey anti-goat antibody coupled to alkaline phosphatase. An NBT/BCIP substrate was used to detect positives. A strong positive band was readily apparent at approximately 46 kDa, the expected size of the fusion protein.

FIG. 5 illustrates the DNA agarose gel electrophoresis test results, an agarose gel showing the DNA used for the DNA vaccine study, along with the control DNA also used in the study. Lane one shows the pVAX1 vector DNA with the hp20 gene inserted in the vector. Lane 2 verifies the presence of the vector without the gene insert. Lane three is the DNA ladder used to demonstrate the approximate sizes of the DNA present.

FIG. 6 illustrates a photograph of a pGEX expression vector showing the Hp20 protein insert. This is a control agarose gel used to demonstrate the successful fusion of the hp20 gene into the pGEX-6P-2 vector. After analysis of the vector/insert construct via agarose gel electrophoresis (FIG. 7), the gene was cleaved out of the vector used the enzymes Not1 and EcoR1. The resulting DNA was then analyzed on an agarose gel (pictured). The gel shows the vector DNA as well as the resulting DNA for the gene which has "dropped" out and is located at approximately 640 bp.

FIG. 7 illustrates a photograph of a pGEX expression vector showing the Hp20 protein insert by analysis of the pGEX-6P-2 vector with the hp20 gene insert via agarose gel electrophoresis. The gel shows the shift in weight of the vector with the gene cloned in. This gel serves as a control for the gel shown in FIG. 6 (after the gene was removed), to demonstrate the gene is unmistakably present within the vector.

FIG. 8 illustrates the worm burdens of both sexes compared to the initial challenge. This figure shows the worm burdens found in mice immunized with either: 1) the hp20 gene within the pVAX1 construct, 2) the pVAX1 construct only, as a control, 3) phosphate buffered saline (PBS) only, as a control. This study indicated mice immunized with the vector itself, which has been shown to act as an adjuvant, had a higher worm burden than those that received PBS only. However, those mice that received the hp20 gene within the vector had a lower worm burden after parasite challenge. In addition, we found these results were dependent on the sex of the mice, with female mice responding to hp20-immunization with a decreased burden (compared to control B) and male mice with an increased burden (compared to same control, B).

DETAILS OF THE INVENTION

The methods and procedures for separating, identifying, analyzing the protein complex, the protein having the immuno-suppressive activity and the composition of the recombinantly produced protein complex are provided. The methods and procedures are based on the retrieval of every actively transcribed gene in the *Heligmosomoides polygyrus* (*H. polygyrus*). Each retrieved gene was used to make in vitro complementary sequences identical to the genes within the parasite. Each gene so produced in vitro was placed in a vector to maintain the deoxyribonucleic acid (DNA). The vectors with the so-produced genes were inserted into *E. coli* bacteria to translate the gene into a recombinant protein to represent proteins existing in the original *H. polygyrus* parasites from which the original genes had been retrieved.

A serum containing antibodies to proteins that were excretory/secretory proteins of the *H. polygyrus* parasite was prepared to simulate the physiological conditions present during infection of a host body. The serum was taken from mice immunized with excretory/secretory proteins from the parasite. During infection, the parasites produced proteins that were released in vivo into the surrounding saline of the host body. As these E/S proteins served to immunize mice, any proteins that were immunogenic (capable of combining with antibodies) would elicit an immune response in the subject mice. The serum collected from the immunized mice contained antibodies only to proteins that were E/S proteins actually in contact with the host immune system and elicited an immune response in the host.

The identification of only the proteins that elicited a strong In vivo immune response in the host was made to determine the antibodies in the serum samples collected from the immunized mice as above could bind to the recombinant proteins prepared as above. Twenty-one different *E. coli* bacteria positive colonies containing a recombinant gene from *H. polygyrus* were identified as having encoded an immunogenic protein. All 21 recombinant genes were retrieved from the *E. coli* bacteria and the genetic sequences of each was determined. The determination indicated all 21 recombinant genes contained the same DNA sequence, to indicate an extremely immunogenic in vivo protein. The immunogenic in vivo protein retrieved from the *E. coli* represented a protein produced in the larval stage of the parasite, a stage early in infection actually dwelling within the host tissue. In later infection, during the adult stage, the parasite is dwelling within the host intestinal lumen and would not be in direct contact with the host immune system. It is essential therefore for the larvae stage, as a source to identify the immunogenic protein, be chosen to monitor the development of immunomodulation occurring in the host during parasitic infections since an immunomodulatory protein would need to be an E/S protein or it could not reach a host immune system to alter it in vivo and a protein acting in this capacity is imperatively produced early on in infection to set up the chronic infection and the type of immune response mounted by the host.

The DNA sequence of the protein encoded by the gene was used to screen a computer-based compilation of known genetic sequences, a genbank, to find a genetic homologue, i.e., a related/similar gene in another parasite that would predict what the gene encoded. A genetic homolog of known genetic sequences as recorded in a computer-based compilation of known genetic sequences was not found.

The reading frame of the recombinant gene of the recombinant protein produced thereby was determined to learn which DNA bases were used to make amino acids and what was the sequence of the protein encoded by the gene. Determination of the reading frame permitted prediction of the amino acid sequence of the recombinant protein produced from the recombinant gene.

The amino acid sequence was analyzed via computer modeling. The first study performed showed the exact molecular weight of the recombinant protein. This was confirmed by SDS-PAGE (see FIG. 1), a method of separating and analyzing proteins based on size. The models determined the size of the native protein, the protein size when produced by the parasite. The modeling indicated the protein had a leader sequence, a sequence in front of the protein that allowed the protein to be transported to the surface and subsequently released from the host. The leader sequence confirmed previous evidence that the recombinant protein is an excretory/secretory (E/S) protein.

The cleavage site was identified as occurring exactly at the end of the leader sequence comprising a recognition sequence for an enzyme to cleave the Hp20 protein into two pieces. Identification of the cleavage site demonstrated the leader sequence could be removed after the protein had been transported to the surface. Identification of the cleavage site allowed determination of the exact size of the recombinant protein produced but also the size of the native protein produced by the organism in vivo, since the leader sequence would not be part of the native protein when produced by the organism in vivo during infection.

The amino acid sequence (see EXAMPLE V) was used to search the genbank again to determine if there were any known protein homologues. No matches with homologous or close identities were found. The search indicated the Hp20 protein was of a particular family of proteins, a novel group of fatty acid and retinol binding (FAR) proteins entirely alpha-helical in structure.

A computer program was used to predict the secondary structure of the protein as to how the amino acids aligned themselves. The modeling (see FIG. 2) indicated that Hp20 protein was entirely alpha-helical, arranged as a helix, as DNA. A tertiary structure analysis of the overall structure of the Hp20 protein predicted that the protein was globular like a ball. The modeling indicated the Hp20 protein sequence maintains its secondary and tertiary structures although dissimilar in sequence to other nematode FAR proteins. The maintenance of the secondary and tertiary alpha-helical structures indicates strongly the Hp20 protein and its alpha-helical structure are essential for survival of the parasite.

The initial recombinant version of the Hp20 protein so produced could not be analyzed in depth because it was not isolated. A gene fusion system was selected using a pGEX vector to isolate the protein, GST Gene Fusion System, $3^{rd}$ Edition, Revision 2, Pharmacia Biotech. The system adds another protein into the N-terminus, or beginning, of the protein. The addition of the protein, known as glutathione-S-transferase (GST) allows for the isolation of the Hp20 protein after the protein is expressed and solubilized. The hp20 gene was inserted in the pGEX vector, with the gene read in the correct reading frame (see FIG. 3), translated into the corrected amino acids as verified by DNA sequencing. The vector was then inserted into a protease-deficient strain of E. coli, proteases being enzymes that degrade proteins. The E. coli was used to produce the desired recombinant protein. The E. coli cells were lysed open to release both the proteins belonging to the bacteria and the Hp20 protein complex with the GST protein bound to it. The Hp20 protein complex was mixed with hundreds of other proteins and was insoluble.

An established protocol, Frangioni, et al., Analytical Biochemistry 210, 179-187 (1993), was used to solubilize the protein so the protein could be retrieved. The GST protein attached to Hp20 protein is able to bind glutathione. The binding affinity of GST for glutathione permits the GST-Hp20 protein complex to be separated from hundreds of other proteins in a liquid. The addition of glutathione-sepharose beads, sepharose beads with glutathione attached, permits the GST protein attached to the Hp20 protein to bind to the glutathione. The weight of the beads pulls the desired GST/Hp20 protein complex to the bottom of the liquid. A saline solution washed the other proteins away. Addition of free glutathione solution causes the GST/Hp20 protein complex to be released from the beads. Only the GST/Hp20 protein complex is released into the buffer solution.

Analysis of the retrieved protein was performed by SDS-PAGE. Staining of the protein was with Commassie blue to stain the protein by binding to certain amino acids. The recombinant protein complex had a molecular weight of approximately 46 KDa, comprised of 26 KDa GST and 20 kDa Hp20 protein. The SDS-PAGE showed only one protein band, indicating the protein was isolated.

The SDS-PAGE analysis was followed by western blot analysis using a commercially available antibody to show the isolated protein at 46 kDa was, in fact, the recombinant protein with the GST protein at the N-terminus. The western blot analysis (see FIG. 4) gave a positive result for the protein at 46 kDa.

The following examples illustrate the present invention and methods of defining the composition, the methods and procedures for separation and analyzing the protein having immuno-suppressive activity.

Example I

Process of Protein Production

The following illustrates the process of protein production. The gene ecoding Hp20 protein was removed from a vector into which it was previously cloned, by restriction using the Not 1 and EcoR1 enzymes. The same restriction enzymes were then used to restrict the fusion vector, pGEX-6P-2 (see attached plasmid genome) (see FIG. 3), to make unidirectional, cohesive ends.

The DNA samples were then run on a TAE agarose gel, stained with Ethidium bromide and visualized briefly with UV light. The bands corresponding to the linarized vector and the hp20 gene were retrieved from the gel, cleaned using a standard 'PCR clean-up kit' and the resulting DNA was quantitated using a UV spectrophotometer (see FIG. 5).

The hp20 gene was then ligated into the pGEX-6P-2 vector. The resulting construct was transformed into E. coli DH10B (see FIG. 6). The plasmid construct was then retrieved from the DNA and analyzed on a TBE agarose gel to verify its presence within the bacteria. The construct was then transformed into E. coli BL21, a protease deficient bacteria strain, which could be used for protein expression. The construct was once again removed using a standard plasmid preparation, run on a standard TBE agarose gel, stained with ethidium bromide and analyzed under UV light (see FIG. 7).

Once the presence of the construct in E. coli BL21 was confirmed, the bacteria were used to inoculate approximately 20 ml of LBA (Luria Bertani broth with 100 ug/ml ampicillin) to produce an overnight culture. The overnight culture was then used to inoculate two 500 ml cultures which were then induced with 1 mM IPTG for 34 hours at 37 degrees C. The cells were then transferred to 500 ml centrifuge tubes and centrifuged and pelleted. The cells were resuspended in ice-cold STE containing 600 ug/ml of lysozyme (added immediately prior to resuspension).

The following reagents were then added RNAse, DNAse, dithiothreitol (DTT), leupeptin, and pepstatin. Bacteria were lysed by the addition of sarkosyl to a final concentration of 1.5% from a 10% stock in STE. The cells were vortexed for 5 seconds and incubated on ice for 30-45 minutes. The lysate was centrifuged and transferred to a new tube. Triton X-100 was added to a final concentration of 3% from a 10% stock in STE. The lysate was then added to a 50% glutathione agarose bead solution in PBS. The solution was incubated at room temperature for 45 minutes and washed 6-8 times with sterile 4 degrees C PBS by centrifugation and disposal of subsequent PBS solutions. After removal of the last PBS supernatant from the washes, the pellet was washed with ice cold elution buffer (pH 8.0, 50 mM Tris-HCl, 20 mM reduced glutathione).

The Hp20 protein when produced by the pGEX-6P-2 vector is produced as a fusion protein with the GST (glutathione S-transferase) attached to the N-terminus of the protein. The purified protein was then analyzed on an SDS-PAGE (sodium dodecyl sulfate polyacrylamide gel electrophoresis) and stained using Coommassie blue. One band at 46 kDa was obtained (GST fusion=26 kDa, Hp20 protein, 20 kDa).

The protein was then analyzed by western blot. The protein was blotted to a PVDF membrane and probed with goat anti-GST as the primary antibody and donkey anti-goat as the secondary antibody. One band was obtained at 46 kDa, once again verifying the isolation of the GST-Hp20 protein complex.

The following illustrates the procedure of the DNA vaccine study. pVAX1 plasmid was used as the vaccine vector. The gene encoding Hp20 protein was cloned into the vector and the construct was then transformed into E. coli DH10B. The E. coli were grown up and the cells lysed to release the plasmid constructs. Promega Wizard megapreps were used to isolate the DNA vaccine constructs. The DNA was verified by TBE agarose gel electrophoresis to confirm its integrity. Three groups of inbred balb/c mice were used, all mice in each group were age-matched and sex-matched. Serum samples were collected from all mice prior to implementation of the vaccination schedule. Mice in group "A" were vaccinated with the pVAX1/Hp20 protein DNA construct. Mice in group "B" were vaccinated with the pVAX vector only. Mice in group "C" were given saline only. Mice were immunized intramuscularly (IM). DNA was solubilized originally in dH20 followed by dilution in saline to a final concentration of 0.9% NaCl.

Mice were immunized on days 0, 14, and 28. Serum samples were retrieved prior to immunization, in addition to 10 days post-immunization (each immunization). On day 42 mice were infected with approximately 157 HpL3. On day 63 serum samples were removed and the mice were euthanized. The intestines were slit open lengthwise. The intestines were cleaned by sliding a clean, glass microscope slide along the intestines followed by dipping the intestines in deionized water. The intestines were then placed in toole that was suspended in a beaker of DMEM at 37 degrees C. The H. polygyrus migrated out of the intestines and into the bottom of the beaker. After 3.5 hours the worms were collected and counted. Remaining intestines and toole were also screened for H. polygyrus in the event that some did not make it out into the DMEM. The worm burdens (number of H. polygyrus recorded in each group) are recorded below.

Experimental Group A males: 63

Experimental Group A females: 179

Control males group B: 46

Control females group B: 116

Control males group C: 44

Control females group C: 170

Example III

The following illustrates the procedure of the DNA vaccine study. The DNA vaccine study was performed by injected naked DNA into the mice muscle tissues. The host cells (most likely the myocytes) take up the DNA and begin protein production which acts to immunize the mice. Three groups of genetically identical mice were separated by gender and experimental group. Group A received the pVAX1 vector with the hp20 gene insert. Group B received the pVAX2 vector in saline. Group C received saline only.

Preparation of the Vector and Vector/Insert:

E. coli containing the plasmid of interest was grown and the DNA was extracted by plasmid preparation. The DNA was ethanol precipitated and the DNA purity was assessed by UV spectrophotometry and gel electrophoresis.

Serum collected was performed by tail bleeding of the mice. Serum samples were stored according to group and sex of mice.

Immunization Protocol:

The area of the mice quadriceps was cleaned with a sterile alcohol pad. 50 ug of the appropriate DNA sample, suspended in saline, was delivered to each hind leg of each mouse (for a total of 100 ug per mouse). Group C received an equal volume of saline only. The immunization was repeated every two weeks, for a total of three immunizations.

Challenge Infection:

Two weeks after the third and final immunization, mice were challenged orally with approximately 157 L3 H. polygyrus.

H. polygyrus Retrieval:

21 days after the challenge infection, mice were euthanized in a $CO_2$ chamber. The small intestines were removed and slit lengthwise from the duodenum to the large intestines. After cleaning the intestines in dH20, they were added to toole-lined beakers that were filled with 37 degrees C. Dulbecco's Modified Eagle's Medium. The beakers were incubated for approximately 3.5 hours. The toole and intestines were then removed, the contents allowed to settle, and the worms washed 4 times in sterile PBS. The worms were then pipetted in increments onto slides and counted under a dissecting scope. The toole was also screened for any H. polygyrus not retrieved in the beakers.

Example IV

Example IV illustrates the increase in worm burdens of both sexes of mice that received the vaccine. What was found was a increase in worm burdens of both sexes for mice that received the experimental vaccine. In addition, a dramatic difference was detected in worm burdens when comparing the males vs. females across all three groups. FIG. 8 illustrates the worm burden compared to initial challenge.

Example V

Example V illustrates the amino acid sequence of Hp20 protein. The following is the amino acid sequence of HP20 protein:

(SEQ ID NO: 1)
```
Met L R L G F L A L L I V C V C S T P I K K A E D
I P Q E V R E V L P E N V V Q L I L S F T P A E K
K V I E E F F N N W E K F K T E D E A L N F F K E
K S P S L Y A K I E N L R E I L K K K V A T L S P
E S K A F F D K V Q S S L K D L H K Q I L V G D A
P S L D Met F R E V L R K H V D T Y K A L S A D S
K K E L K K T F P I A A R V Met S K L V G S N Stop
```

Example VI

Example VI illustrates the gene sequence of the hp20 gene comprising the DNA gene sequence of the 21 recombinant genes from *H. polygyrus* of a biologically functional protein of molecular weight of 20 kDa:

(SEQ ID NO: 2)
```
CCCGGGTCGACCCAGCGTCCGCAAGAATGCTTCGSCTTGGGTTCTTAGCA
CTTCTGATCGTCTGTGTTTGTTCCACGCCTATCAAAAAAGCCGAAGACAT
TCCACAGGAAGTCAGAGAGGTGCTGCCAGAAAACGTGGTTCAGTTGATCC
TCTCATTCACACCAGCCGAGAAGAAGGTCATTGAGGAGTTCTTCAACAAT
TGGGAAAAGTTCAAGACCGAAGATGAGGCACTGAACTTCTTCAAAGAGAA
ATCGCCCTCCCTATACGCAAAAATTGAGAACCTACGCGAGATCCTCAAAA
AGAAGGTCGCTACTCTCAGCCCGGAGTCAAAGGCGTTCTTCGACAAGGTT
CAGTCCTCGCTGAAAGACCTGCACAAGCAGATTCTCGTAGGAGATGCACC
TTCGCTGGACATGTTCAGAGAGGTTCTAAGAAAGCACGTAGACACATACA
AGGCACTTTCCGCTGACTCCAAGAAGGAGCTGAAGAAGACCTTCCCTATC
GCAGCCAGAGTGATGAGTAAACTAGTTGGAAGCAACTGAAGACCACTTGT
GGAGTTCCTCGGCTGCAATAACATGTCAATTTTTGGTGGAAATAAATGTA
TCCCTG
```

What is claimed:

1. *Heligmosomoides polygyrus* composition comprising: the isolated polypeptide consisting of the amino acid sequence of: Met Leu Arg Leu Gly Phe Leu Ala Leu Leu Ile Val Cys Val Cys Ser Thr Pro Ile Lys Lys Ala Glu Asp Ile Pro Gln Glu Val Arg Glu Val Leu Pro Glu Asn Val Val Gln Leu Ile Leu Ser Phe Thr Pro Ala Glu Lys Lys Val Ile Glu Glu Phe Phe Asn Asn Trp Glu Lys Phe Lys Thr Glu Asp Glu Ala Leu Asn Phe Phe Lys Glu Lys Ser Pro Ser Leu Tyr Ala Lys Ile Glu Asn Leu Arg Glu Ile Leu Lys Lys Lys Val Ala Thr Leu Ser Pro Glu Ser Lys Ala Phe Phe Asp Lys Val Gln Ser Ser Leu Lys Asp Leu His Lys Gln Ile Leu Val Gly Asp Ala Pro Ser Leu Asp Met Phe Arg Glu Val Leu Arg Lys His Val Asp Thr Tyr Lys Ala Leu Ser Ala Asp Ser Lys Lys Glu Leu Lys Lys Thr Phe Pro Ile Ala Ala Arg Val Met Ser Lys Leu Val Gly Ser Asn (SEQ ID NO:1); and an adjuvant.

* * * * *

SEQUENCE LISTING

<160> NUMBER OF SEQ ID NOS: 2

<210> SEQ ID NO 1
<211> LENGTH: 170
<212> TYPE: PRT
<213> ORGANISM: Heligmosomoides polygyrus

<400> SEQUENCE: 1

```
Met Leu Arg Leu Gly Phe Leu Ala Leu Leu Ile Val Cys Val Cys Ser
1               5                   10                  15

Thr Pro Ile Lys Lys Ala Glu Asp Ile Pro Gln Glu Val Arg Glu Val
            20                  25                  30

Leu Pro Glu Asn Val Val Gln Leu Ile Leu Ser Phe Thr Pro Ala Glu
        35                  40                  45

Lys Lys Val Ile Glu Glu Phe Phe Asn Asn Trp Glu Lys Phe Lys Thr
    50                  55                  60

Glu Asp Glu Ala Leu Asn Phe Phe Lys Glu Lys Ser Pro Ser Leu Tyr
65                  70                  75                  80

Ala Lys Ile Glu Asn Leu Arg Glu Ile Leu Lys Lys Lys Val Ala Thr
                85                  90                  95

Leu Ser Pro Glu Ser Lys Ala Phe Phe Asp Lys Val Gln Ser Ser Leu
            100                 105                 110

Lys Asp Leu His Lys Gln Ile Leu Val Gly Asp Ala Pro Ser Leu Asp
        115                 120                 125

Met Phe Arg Glu Val Leu Arg Lys His Val Asp Thr Tyr Lys Ala Leu
    130                 135                 140

Ser Ala Asp Ser Lys Lys Glu Leu Lys Lys Thr Phe Pro Ile Ala Ala
145                 150                 155                 160

Arg Val Met Ser Lys Leu Val Gly Ser Asn
                165                 170
```

```
<210> SEQ ID NO 2
<211> LENGTH: 605
<212> TYPE: DNA
<213> ORGANISM: Heligmosomoides polygyrus

<400> SEQUENCE: 2
cccgggtcga cccagcgtcc gcaagaatgc ttcgscttgg gttcttagca cttctgatcg      60
tctgtgtttg ttccacgcct atcaaaaaag ccgaagacat tccacaggaa gtcagagagg     120
tgctgccaga aaacgtggtt cagttgatcc tctcattcac accagccgag aagaaggtca     180
ttgaggagtt cttcaacaat tgggaaaagt tcaagaccga agatgaggca ctgaacttct     240
tcaaagagaa atcgccctcc ctatacgcaa aaattgagaa cctacgcgag atcctcaaaa     300
agaaggtcgc tactctcagc ccggagtcaa aggcgttctt cgacaaggtt cagtcctcgc     360
tgaaagacct gcacaagcag attctcgtag gagatgcacc ttcgctggac atgttcagag     420
aggttctaag aaagcacgta gacacataca aggcactttc cgctgactcc aagaaggagc     480
tgaagaagac cttccctatc gcagccagag tgatgagtaa actagttgga agcaactgaa     540
gaccacttgt ggagttcctc ggctgcaata acatgtcaat ttttggtgga aataatgtat     600
ccctg                                                                605
```